US011357559B2

(12) United States Patent
Heuer (10) Patent No.: US 11,357,559 B2
(45) Date of Patent: Jun. 14, 2022

(54) MODULAR OSTEOSYNTHESIS DEVICE FOR VERTEBRAE

(71) Applicant: MIMEO medical GmbH, Filderstadt (DE)

(72) Inventor: Frank Heuer, Filderstadt (DE)

(73) Assignee: MIMEO MEDICAL GmbH, Filderstadt (DE)

( * ) Notice: Subject to any disclaimer, the term of this patent is extended or adjusted under 35 U.S.C. 154(b) by 0 days.

(21) Appl. No.: 17/334,303

(22) Filed: May 28, 2021

(65) Prior Publication Data

US 2021/0369315 A1    Dec. 2, 2021

(30) Foreign Application Priority Data

May 29, 2020    (DE) .................... 10 2020 003 247.8

(51) Int. Cl.
*A61B 17/70* (2006.01)
*A61B 17/86* (2006.01)

(52) U.S. Cl.
CPC ...... *A61B 17/8685* (2013.01); *A61B 17/7032* (2013.01); *A61B 17/7037* (2013.01)

(58) Field of Classification Search
CPC ............ A61B 17/8685; A61B 17/7032; A61B 17/7035; A61B 17/7037; B33Y 80/00; A61F 2002/30985; B22F 10/00
USPC ....... 606/265, 266, 267, 270, 278, 305, 306, 606/308, 328
See application file for complete search history.

(56) References Cited

U.S. PATENT DOCUMENTS

| | | | |
|---|---|---|---|
| 2006/0149244 A1* | 7/2006 | Amrein | A61B 17/7037 606/264 |
| 2006/0200128 A1 | 9/2006 | Mueller | |
| 2008/0269742 A1* | 10/2008 | Levy | A61B 17/7032 606/60 |
| 2010/0114180 A1* | 5/2010 | Rock | A61B 17/7037 606/308 |
| 2011/0276098 A1* | 11/2011 | Biedermann | A61B 17/7037 606/305 |
| 2012/0283789 A1* | 11/2012 | Biedermann | A61B 17/7034 606/308 |
| 2014/0277163 A1 | 9/2014 | Kretzer et al. | |
| 2015/0119940 A1* | 4/2015 | Jackson | A61B 17/7037 606/266 |
| 2018/0214183 A1* | 8/2018 | Heuer | A61B 17/7038 |
| 2019/0008562 A1* | 1/2019 | Melton | B22F 10/00 |

(Continued)

FOREIGN PATENT DOCUMENTS

| | | |
|---|---|---|
| DE | 698 13 290 | 1/2004 |
| DE | 10 2015 214 384 | 2/2017 |
| DE | 10 2018 102 173 | 6/2019 |

*Primary Examiner* — Eduardo C Robert
*Assistant Examiner* — David C Comstock
(74) *Attorney, Agent, or Firm* — Nixon & Vanderhye P.C.

(57) ABSTRACT

An osteosynthesis device for the treatment of the spine is disclosed having a fork head which is U-shaped in a side view, and which fork head, in the proximal direction, has two fork legs with an internal thread and in which a connecting rod can be received, and a grub screw is passed through the internal thread, and the fork head is detachably connected to a bone anchor. The bone anchor is pivotably mounted in the ball seat of the fork head, wherein the fork head in the ball seat area has slots open towards the distal side and thereby at least one deflectable leg is formed.

19 Claims, 12 Drawing Sheets

(56) References Cited

U.S. PATENT DOCUMENTS

2019/0150989 A1\* 5/2019 Biester ............... A61B 17/8615
2020/0121367 A1 4/2020 Biedermann \* cited by examiner

MODULAR OSTEOSYNTHESIS DEVICE FOR VERTEBRAE

CROSS RELATED APPLICATION

This application claims priority to German Patent Application DE 10 2020 003 247.8, filed May 29, 2020, the entire contents of which is hereby incorporated by reference.

PRIOR ART

Various osteosynthesis devices for supplying the spine, such as pedicle screws, are known in the prior art. Such osteosynthesis devices are used to correct spinal deformities or to stabilize fractures by inserting the osteosynthesis devices into the vertebral bone and fastening them and then connecting them to one another via longitudinal rods, or so-called connecting rods, in order to fix the vertebrae in a desired position. For this purpose, the longitudinal rods are mounted on the osteosynthesis devices with the help of grub screws and fixed in a non-slip manner pedicle screws are preferably used as osteosynthesis devices, which pedicle screws have a bone anchor which is pivotably mounted polyaxially with a fork head and is angularly stable when the grub screw is fixed. Bone screws with a spherical head are preferably used as bone anchors. Osteosynthesis devices with bone anchors and fork heads are normally mounted in such a way that the bone anchor, coming from the proximal side, is passed into the fork head and the bone anchor shaft is passed through the distal opening of the fork head. This only works if the outer diameter of the bone anchor shaft is smaller than the spherical head diameter of the bone anchor, and the outer diameter of the bone anchor shaft is smaller than the diameter of the distal opening of the fork head. Assembly is problematic if the outer diameter of the bone anchor shaft is larger than the opening diameter of the fork head and/or the spherical head diameter of the bone anchor.

A construction of a pedicle screw is known from the prior art, for example from US20060200128A1 or US2020121367A1, in which the fork head coming from the distal side can be mounted with a bone anchor. In this case, the fork head is constructed of multiple pieces and has a kind of clamping cage or collet chuck in the distal fork head area. Often three or more components are required. A multi-piece construction of a bone anchor affects adversely the mechanical stability and maximum load capacity. Overloading can lead to disassembly and thus to premature implant failure. From a manufacturing point of view, the tight tolerances of all components must be adhered to and checked at all times. This makes the production complex and costly. A one-piece construction of the fork head is therefore desirable. Furthermore, pedicle anchors (DE102018102173B3) are known the prior art which can be locked temporarily and thus enable an enhanced application spectrum in the care of spinal instabilities. Such an arrangement is technologically complex and expensive from the point of view of manufacture. Therefore, it is desirable to provide as little as possible components, to implement a temporary clamping capacity, to reduce the assembly steps while optimizing the manufacturing costs at the same time.

SUMMARY OF THE INVENTION

This is achieved by the osteosynthesis device according to the invention. The osteosynthesis device consists of a fork head which is U-shaped in a side view, and which fork head, in the proximal direction, has two fork legs with an internal thread and in which a connecting rod can be received, and a grub screw is passed through the internal thread, and the fork head is detachably connected to a bone anchor, and the bone anchor is pivotably mounted in the ball seat of the fork head, wherein the fork head in the ball seat area has slots open towards the distal side and thereby at least one deflectable leg is formed. The leg or legs is/are in contact with an outer surface of the bone anchor head, wherein the at least one leg has an outer wall and an inner wall, which are interconnected at at least one point in such a way that upon tightening the grub screw, a pressing against one another of the outer wall and the inner wall from the proximal to the distal direction is generated, so that a compressive stress arises in the outer wall and a tensile stress arises in the inner wall, whereby the at least one deflectable leg is forced against the outer circumference of the spherical head and as a result, the spherical head of the bone anchor clamps in the fork head at a stable angle due to the resulting compressive force.

Furthermore, the fork head is also suitable for receiving different rod diameters.

Preferably, bone screws are used as bone anchors which bone screws can be screwed onto a bone. However, hooks, clamps, nails and bone anchors of different designs can also be used. The essential features of the bone anchor are a ball-like head, a neck area and an area which can be anchored or fastened in or at the bone.

By a corresponding arrangement of the outer and inner walls of the deflectable legs, the bone anchors can be mounted relatively easily on the fork head by placing or pressing them on said fork head. The bone anchor can also be removed again using an aid, such as a release instrument. The osteosynthesis device according to the invention can thus be configured in a modular fashion by the user and assembled in the operating room at a later point in time than that of manufacture. The advantage is that on the one hand larger bone anchors, i.e. bone anchors with a larger outer diameter than the distal inner diameter of the fork head, can be mounted. On the other hand, the bone anchor portfolio can be minimized, since the user can combine fork head and bone anchor during surgery instead of resorting to a prefabricated oversized portfolio. Such a portfolio must be on hand at the user and thus is tying up more capital than the modular version of the invention would require.

As already described, the osteosynthesis device can be mounted relatively easily by clicking the bone anchor into the fork head coming from the distal side. If a connecting rod is inserted, which is then fixed with the grub screw and subjected to force, a clamping effect arises in the fork head, so that the bone anchor is fixed or clamped in the fork head, in particular a ball seat. The clamping is thus initialized in that the connecting rod pushes on at least one outer rod support and thus acts on the outer wall with a pressure force and compressive stresses are dissipated along the outer wall, which in turn result in tensile stresses of the inner wall and thereby a pulling against one another is generated and said pulling against one another generates a radially inwardly directed movement of the deflectable leg. Said radially inwardly directed movement of the deflectable leg is limited by the spherical head, whereby no movement is created but a clamping force is created.

In an alternative embodiment, it is possible to initiate the clamping effect via a projection or contact point on the outer wall without the connecting rod or the grub screw being present. Since this is not a final clamping with inserted connecting rod, this kind of clamping is called temporary clamping. With the temporary clamping it is possible for the user to convert a polyaxial screw in a desired angular position into a monoaxial screw during surgery. This means that all rotational degrees of freedom of a polyaxial screw are temporarily blocked. The screw behaves monoaxially. This means that the user can now manipulate the vertebra to be treated in translatory as well as rotatory fashion until said user inserts a connection rod in the desired final position and fixes it with the grub screw. Such correction maneuvers are not possible with a polyaxial screw, since a correction maneuver initiated by the patient on the outside results in a free movement of the polyaxial ball joint and is therefore not passed on to the vertebra. This only works with deactivated rotational degrees of freedom in the ball joint, that is to say, is clamped temporarily.

When the outer wall is tensioned against the inner wall, a high elastic deformation of the walls occurs, this tension being maintained in a spring-like manner. This has the great advantage that if the clamped bone anchor should move in the event of excessive stress, the clamp does not loosen, but rather restores the same resistance of the clamp in the forced new position. Conventional pedicle screws experience a micro-misalignment between the components when they are overstrained, which leads to an immediate reduction in stress and loosens the polyaxial connection because they do not have any resilient components.

Another advantage of this arrangement of inner wall and outer wall as well as the connection point is that this force introduction maneuver can also be used in reverse. This means that with the reverse force introduction maneuver it is possible to open the ball seat area of the fork head. This makes it possible to remove the bone anchor from the fork head again. However, an aid such as a surgical instrument is necessary for this purpose. The reverse force introduction maneuver to open the fork head only works without a connection rod. For this purpose, forces must be introduced at other edges or projections in order to be able to carry out the opposite force introduction maneuver. A precise location of these edges or projections can be found in the Figures.

In the unloaded state and when the fork head is clamped, the diameter of the distal fork head opening is smaller than the diameter of the spherical head of the bone anchor. If the maneuver to open the fork head is initiated, the diameter of the distal fork head opening is equal to or greater than the diameter of the spherical head. This allows the bone anchor to be removed from the fork head.

In the circumferential direction at least two slots are required to form a deflectable leg. Of course, it makes sense to provide more than one deflectable leg on the fork head. The slots extend from radially inside to radially outside through the inner wall and through the outer wall and also cut through the connection point. In this case, the slot height of the inner wall and the slot height of the outer wall can be different. Ideally, the slots are rounded in the proximal direction. The slits are open in the distal direction. The maximum of a radially inwardly directed movement of the deflectable legs can be limited by the slot width. This is due to the fact that the width of the slots indirectly defines contact points between the deflectable legs, which in turn determine a movement restriction and thus the maximum inward movement. It can be advantageous for the slots to be arranged unsymmetrically in the circumferential direction. An unsymmetrical arrangement of the slots favors the flow of forces from the outer rod supports to the areas of the proximal outer wall facing away.

A circumferential groove with a hook-like profile is provided in the proximal fork head area, which provides a grip for engaging from behind for an instrument. As a representative, differently designed groove profiles or other holding features such as, for example, openings are conceivable, which provide a grip for engaging from behind for an instrument.

At the proximal end of the fork head there can be further and detachable sections with a threaded area which allow the connecting rod to be repositioned. It is also conceivable that a sleeve-like access formed by two longer legs is provided as used for the minimally invasive access. In this case, the detachable leg extensions can optionally be connected to one another at the proximal end. A detachable connection means, for example, predetermined breaking points that are suitable for removing the extensions after the connecting rod has been finally fixed.

All metallic alloys that are known and accepted as orthopedic implant material are suitable as the material. These include, for example, titanium, cobalt-chromium and stainless steel alloys. The conventional manufacture of the fork head with the outer wall and inner wall connected to one another, so that the legs are formed, is currently not possible or only possible with the greatest technological effort. That is why additive manufacturing is the method of choice. Thus, the fork head can be constructed integrally. Additive manufacturing of metallic alloys, also known as 3D printing, make use of the laser or electron beam melting process.

The long-term success of a 3D-printed implant depends heavily on its follow-up treatment. Targeted heat treatment and surface treatment are extremely important. Relevant literature is available for this purpose, which explains the relationships between the follow-up treatments. Due to the poorly accessible gap between the outer and inner walls, a grinding and blasting process is not effective. With the help of chemical etching, which can optionally be supported by a galvanic voltage and/or by mechanical stimulation, a corresponding reduction in the surface roughness can be achieved. The aim is to free the gap between the outer wall and the inner wall from the incompletely welded particles, since tensile stresses occur here and micro-notches that arise from the incompletely welded particles can mean a weakening of the fatigue strength.

When manufacturing with a 3D printing process, some design parameters must be considered. On the one hand, all structures must have a minimum wall thickness of at least 0.1 mm, or better of at least 0.3 mm and, on the other hand, gaps or slots must have a gap thickness of at least 0.1 mm, or better of at least 0.3 mm, so that during additive manufacturing, the gap also remains open and does not close unintentionally.

BRIEF DESCRIPTION OF THE DRAWINGS

FIG. 6b shows a sectional illustration of FIG. 6a, FIG. 7a shows the alternative embodiment from FIG. 6a in connection with an instrument for the temporary clamping.

DESCRIPTION OF THE PREFERRED EMBODIMENTS

Figure 1:
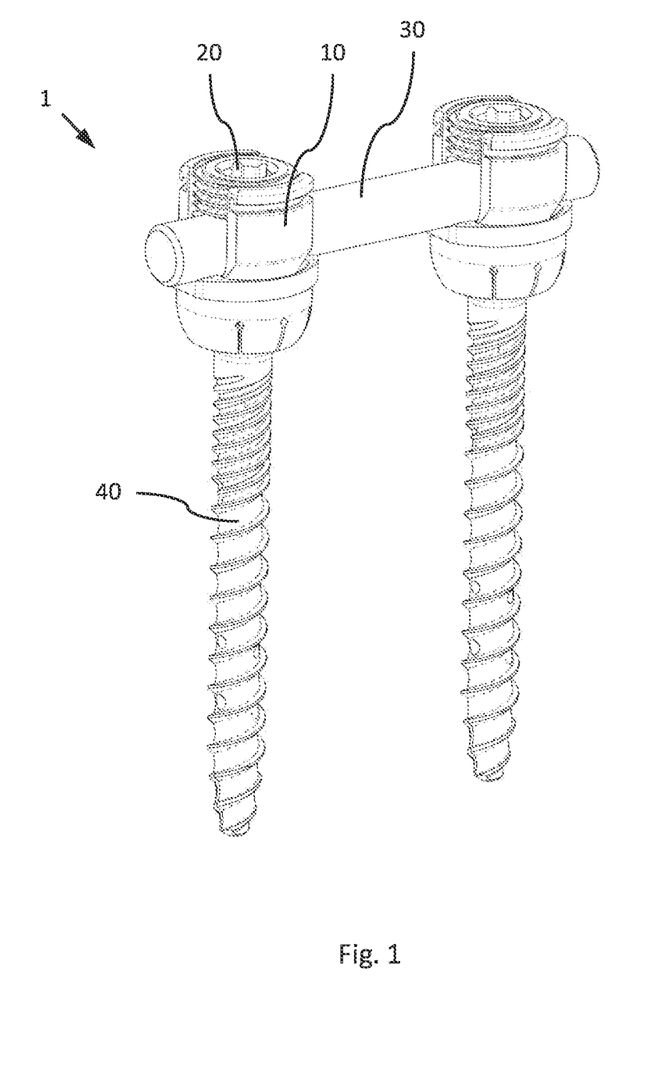
FIG. 1 shows an oblique view of two osteosynthesis devices according to the invention which are connected to a connecting rod.

An osteosynthesis device (1) is described for treating the spine, with more than one osteosynthesis device (1) being used to connect one or more vertebrae with the aid of connecting rods (30) and thus to stabilize the spine (FIG. 1).

Figure 2:
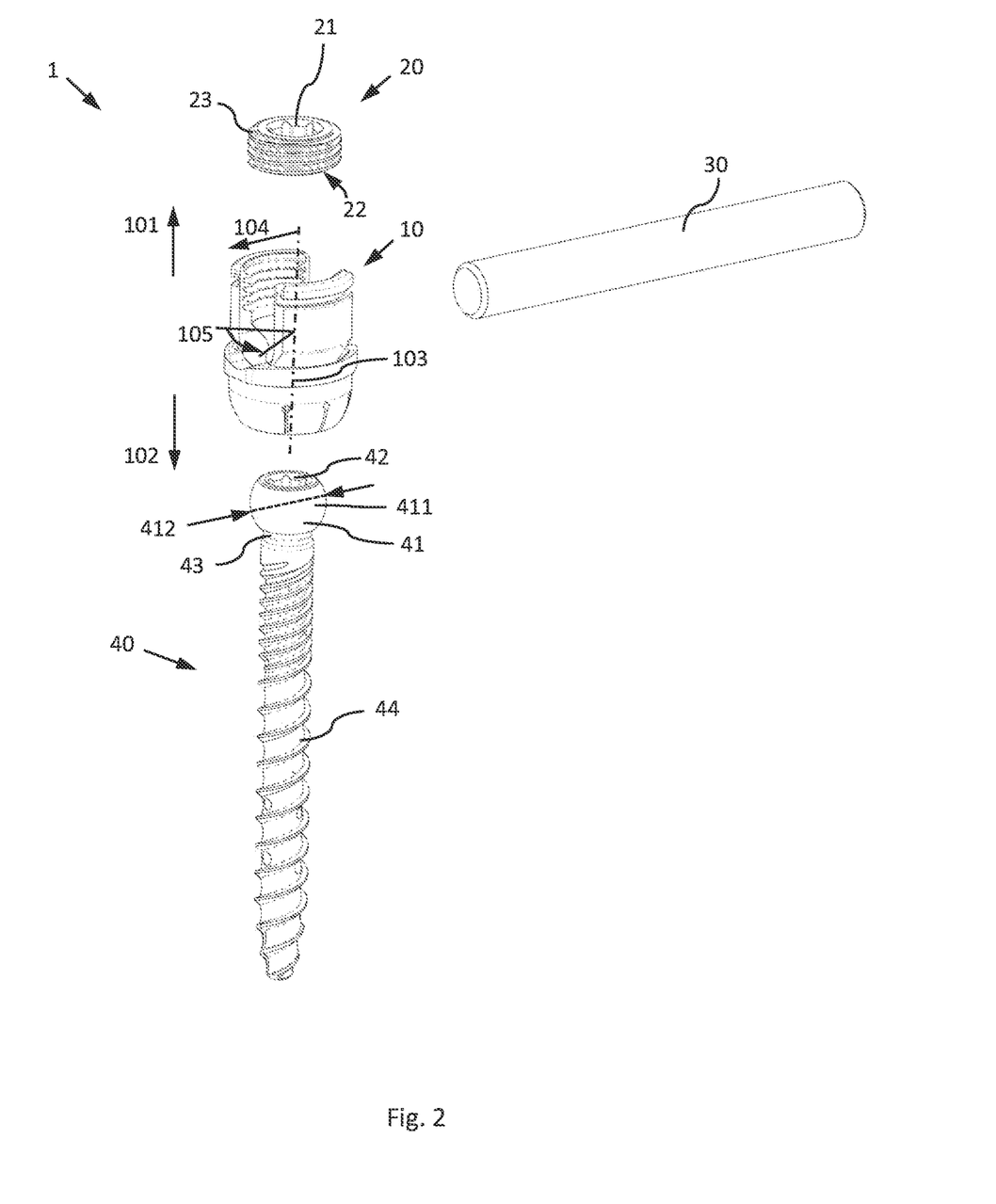
FIG. 2 shows an exploded illustration of an osteosynthesis device according to the invention.

For the osteosynthesis device (1), in particular for the fork head (10), space-assigning coordinate references are defined, such as, for example, the proximal direction (101) and the distal direction (102), which extend along a central axis (103). Starting from the central axis (103) outwards defines the radial expansion (104) and the circumferential expansion (105) is defined by a constant radius and a variable circumferential angle (FIG. 2).

Figure 3A:
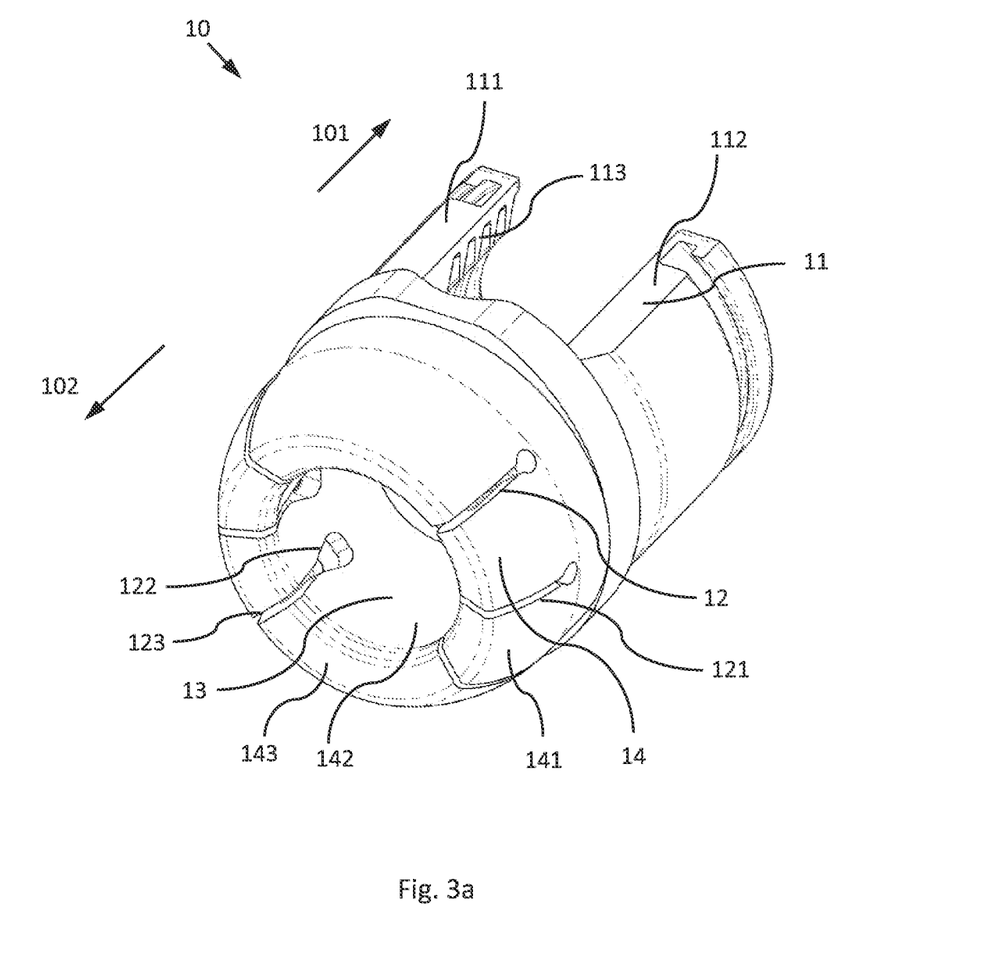
FIG. 3a shows an oblique illustration from the distal side of a fork head.
Figure 3B:
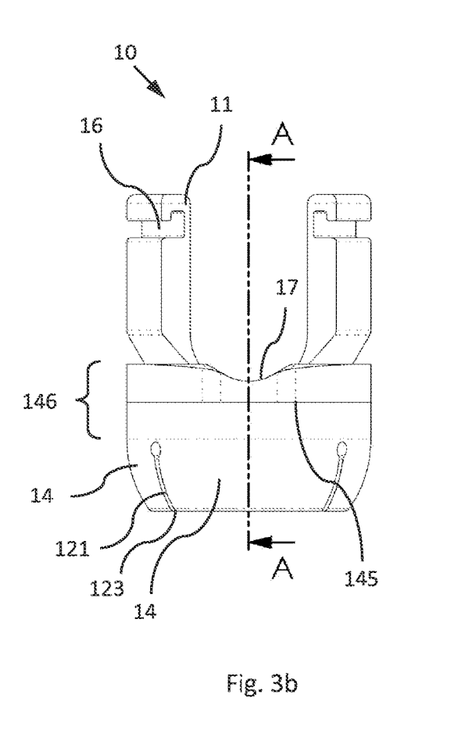
FIG. 3b shows a side view of the fork head.
Figure 3C:
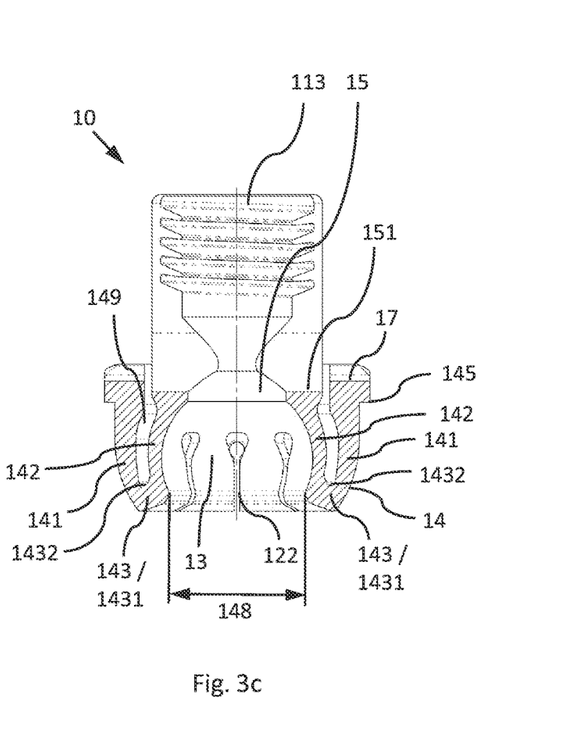
FIG. 3c shows a sectional view of FIG. 3b.
Figure 3D:
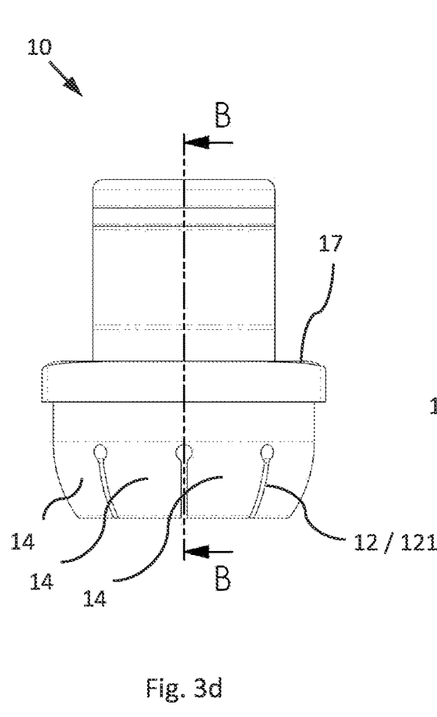
FIG. 3d shows a side view of the fork head, which was created orthogonal to the side view of FIG. 3b.

In this case, the osteosynthesis device (1) has a fork head (10) which is U-shaped in a side view and which fork head (10), in the proximal direction (101), has two fork legs (111, 112) with an internal thread (113) and in which a connecting rod (30) can be received, and a grub screw (20) is passed through the internal thread (113), and the fork head (10) is detachably connected to a bone anchor (40) (FIGS. 1 and 2), and the bone anchor (40) is pivotably mounted in the ball seat (13) of the fork head (10), wherein the fork head (10) in the ball seat area (13) has slots (12, 121, 122, 123) open towards the distal side and thereby at least one deflectable leg (14) is formed (FIG. 3a). Wherein the bone anchor (40) has a head (41), a tool attachment point (42), a neck area (43) and an optional bone thread (44). The head (41) is characterized by a spherical outer surface (411) which can be described by a diameter (412). The grub screw (20) has a tool attachment point (21), an external thread (23) and a distal contact surface (22) which, in the mounted state, is in contact with the connecting rod (30). The external thread (23) of the grub screw (20) preferably has an undercut so that the two fork head legs (111 and 112) do not deform outwardly when the grub screws are tightened.

The one or more deflectable legs (14) each have an outer wall (141) and an inner wall (142) which are connected to one another at at least one point (143) (FIGS. 3b, 3c, 3d and 3e). This connection (143) is preferably formed integrally. Furthermore, it is advantageous if this connection point (143) is in the free end area (1431) of the deflectable leg (14) in order to maximize the deflectability of the leg. Between the inner wall (142) and the outer wall (141) there is a gap (149) which is formed circumferentially (105). The distal end of the gap (149) joins the inner wall (142) with at least one radius (1432). This point is subjected to greater tensile stresses, a radius (1432) being advantageous for better distribution of the loads within the walls. The inside of the inner wall (142) is shaped in such a way that it surrounds the spherical head (41) of the bone anchor (40) in sections and rests against the spherical head outer surface (411). Furthermore, the one deflectable leg (14) is separated by slots (12) at least partially, and the slots (12) separate parts of the outer wall (121, 141), parts of the inner wall (122, 142) and parts of the connection point (123, 143). The slots (12) in this case extend from radially inside (122) to radially outward (121), so that the inner wall (142) and outer wall (141) and the connection point (143) have slots (121, 122, 123). For the redistribution of compressive and tensile stresses, it can be advantageous for the slots (121) in the outer wall (141) to have a different height than the slots (122) in the inner wall (142).

To determine the mechanical properties of the fork head and the clamping capacity, it can be advantageous if the wall thickness of the outer wall (141) is thicker than that of the inner wall (142). In this case, the inner wall (142) should have at least a smallest wall thickness of 0.3 mm and a maximum wall thickness of 1.5 mm, in particular of 0.4 mm to a maximum of 1.0 mm. Furthermore, it has a mechanical advantage if the outer wall (141) of the deflectable leg (14) tapers at least in sections from proximal (101) to distal (102). This can also be promoted if the inner wall (142) of the deflectable leg (14) tapers at least in sections from proximal (101) to distal (102). Furthermore, the proximal area (146) of the outer wall (142) is formed to enclose the fork head (10) fully and ends below the proximal end of the fork head (11). Furthermore, the fork head (10) according to the invention has a central opening (15) through which the screw-in instrument can be passed, with which the bone anchor (40) and the tool attachment point (42) can be subjected to a torque. The fork head has at least two rod supports, at least one inner (151) and at least one outer rod support (17).

Figure 3E:
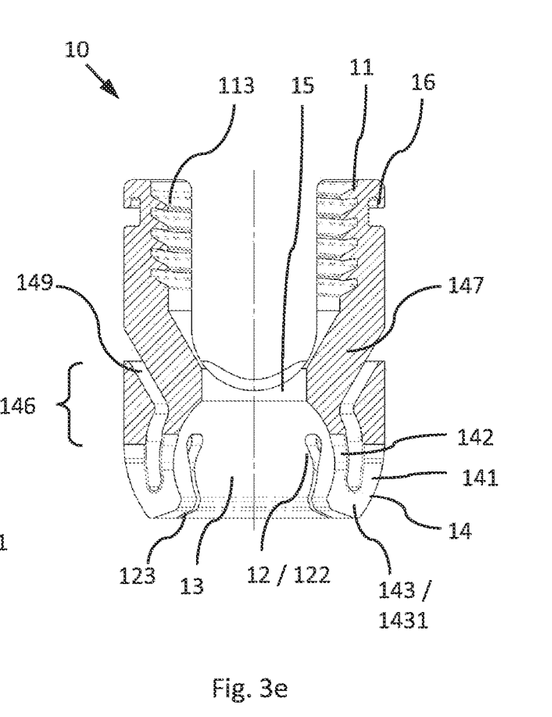
FIG. 3e shows a sectional illustration that was generated from FIG. 3d.

FIG. 3e also shows that the inner walls (142) of the deflectable legs (14) coming from the distal side merge above the ball seat (13) and form the proximal area (147) and the fork legs (11, 111, 112).

Figure 3F:
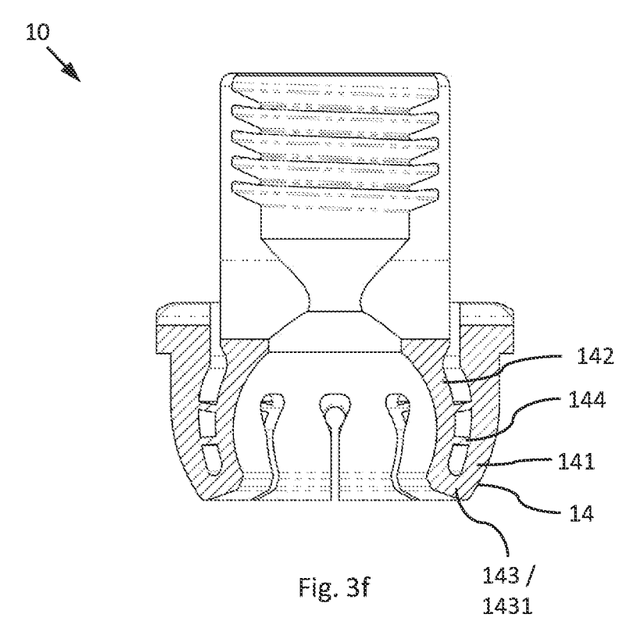
FIG. 3f is a sectional illustration of an alternative embodiment with additional connecting webs.

In an alternative configuration, it can be advantageous if the outer wall (141) and inner wall (142) of the deflectable leg (14) are connected to one another by further struts or supports (144) (FIG. 3f). In this way, the force diversion effect, i.e., the deflection movement of the leg (14), can be increased. It is advantageous if these struts are flexible and mainly active in the pulling direction.

Figure 3G:
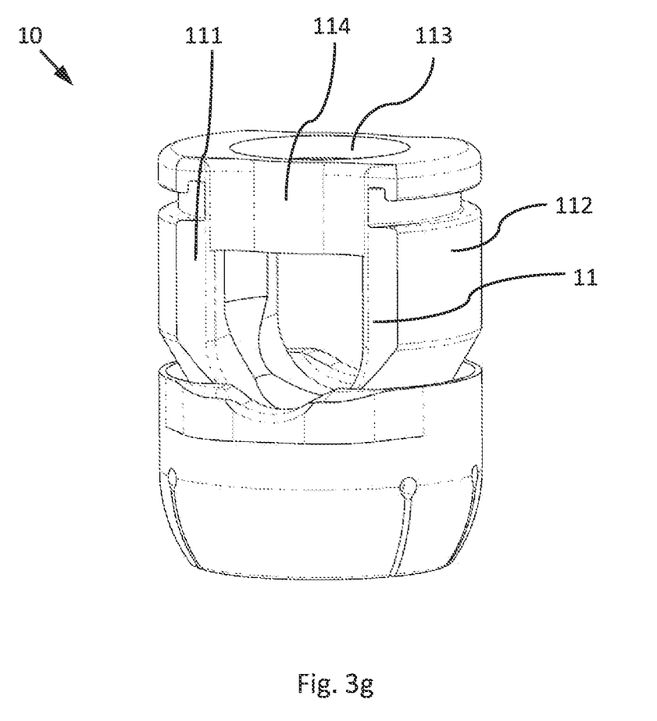
FIG. 3g shows an alternative configuration of the fork head, the two fork legs being connected to one another proximally.

FIG. 3g shows a further configuration in which the fork legs (111, 112) are connected to one another (114) in the proximal area (101) and contain the internal thread (113) when connected. This can be advantageous if the risk of losing the connecting rod is to be minimized. This can be very advantageous, for example, in the case of highly stressed pedicle anchors, to use a fork head (10) that is closed towards the proximal side.

Figure 4:
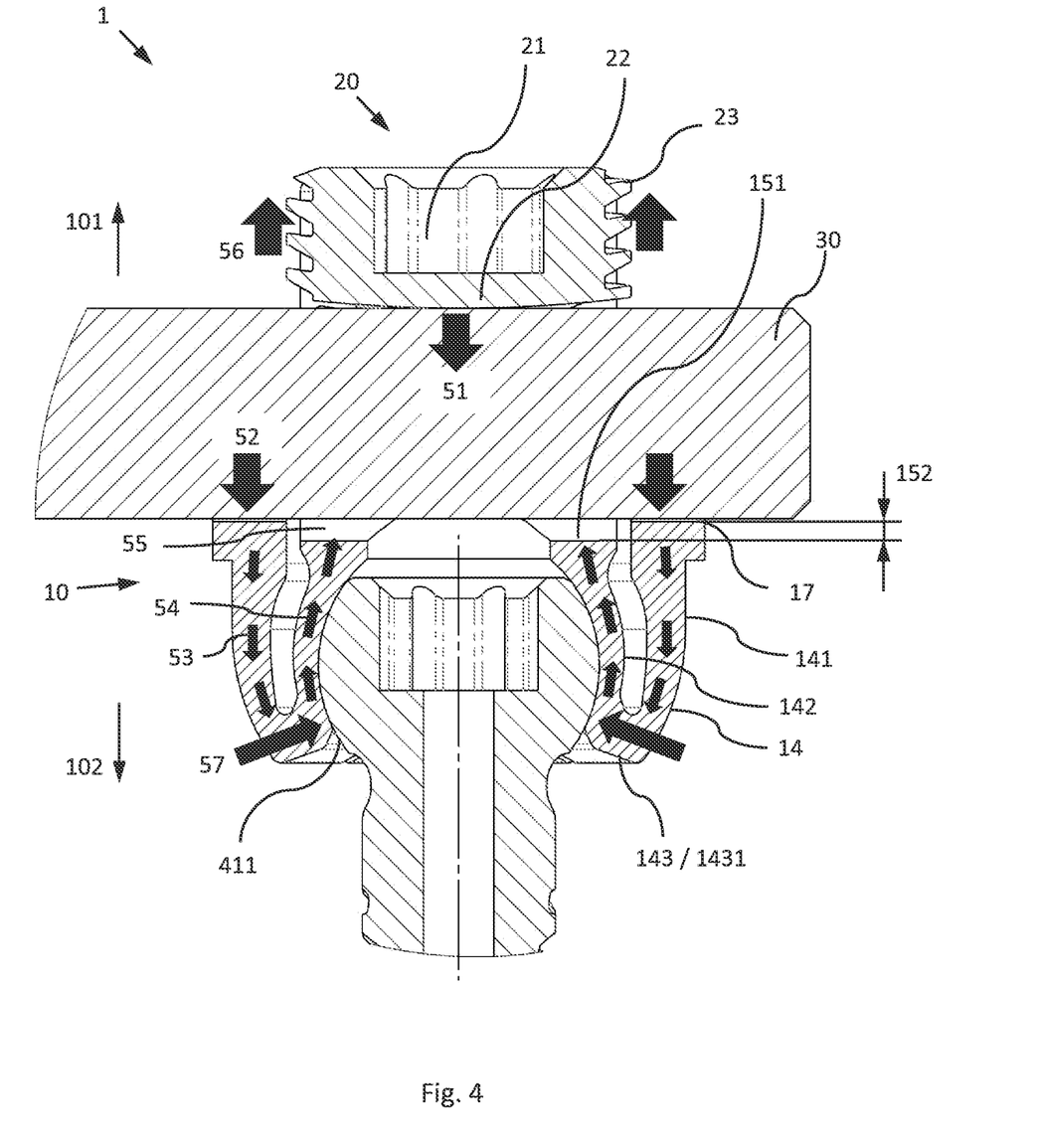
FIG. 4 shows a sectional illustration of the osteosynthesis device in the loaded state forced by the grub screw. The resulting force flow is illustrated.

In the unloaded state, the connecting rod (30) rests on at least one outer rod support (17), the connecting rod (30) being at a distance (152) from at least one inner rod support (151), and in the loaded state with the grub screw (20) tightened, this distance (152) being reduced (FIG. 4). Tightening the grub screw (20) creates a compressive force (51) that presses on the connecting rod (30). The compressive force (51) is transferred (52) to the outer rod supports (17) and transmitted to the outer wall (141). This introduction of force of the grub screw (20) produces a pressing against one another of the outer wall (141) and inner wall (142) from the proximal (101) to the distal (102) direction, so that a compressive stress (53) arises in the outer wall (141) and a tensile stress (54) arises in the inner wall (142), as a result of which the at least one deflectable leg (14) is forced against the outer circumference (411) of the spherical head (41) and, as a result, the spherical head (41) of the bone anchor (40) is clamped in the fork head (10) at a stable angle due to the resulting compressive force (57). As an antagonist of the compressive force (51), which is transferred to the connecting rod (30) by the grub screw (20), a reaction force arises in the thread (56), which results from the pressing against one another between the outer and inner walls (141, 142) (55) from the tensile stress.

Figure 5:
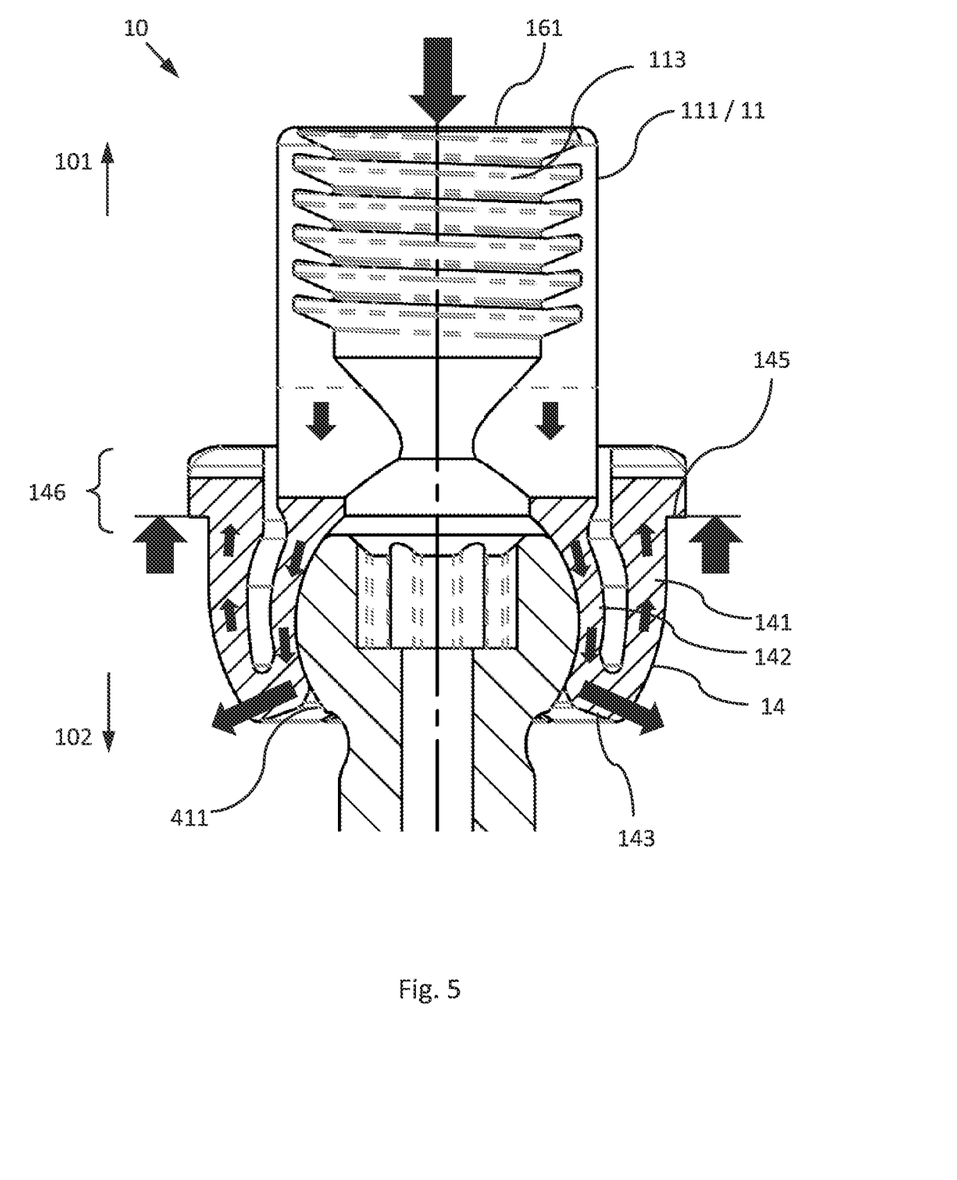
FIG. 5 shows a sectional illustrated in the reverse loaded case, when the fork head is opened distally.

With the arrangement of the outer and inner walls (141, 142), the opposite loading condition is also possible, namely the opening of the distal ball seat (13) and thus enlarging the diameter (148). This works as follows. The fork head (10) in the area of the fully enclosing outer wall (146) has at least one distally directed edge or projection (145) (FIG. 5). Furthermore, the fork head (10) has at least one proximally directed edge or projection (161) which can be used as a counter bearing in order to initiate an opposing force acting on it. In this case, the edges or projections can be chosen as desired. It is only important that a relative movement in the opposite direction is generated between the outer wall (141) and the inner wall (142). If a pulling against one another of the outer wall (141) and inner wall (142) is generated according to FIG. 5, a compressive stress arises in the inner wall (142) and a tensile stress arises in the outer wall (141), which lead to the at least one deflectable leg (14) moving away from the outer surface (411) of the bone anchor head (41).

Figure 6A:
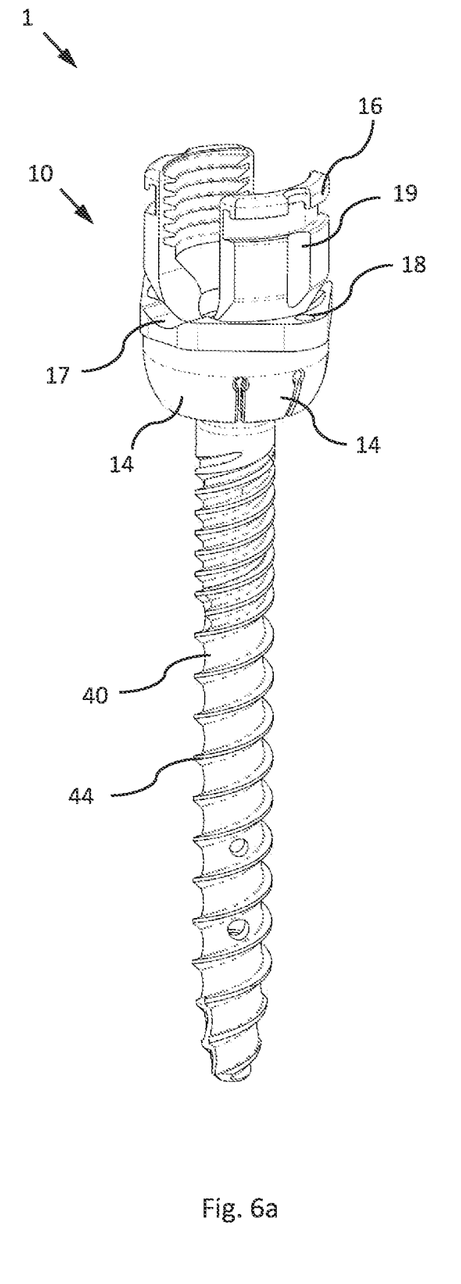
FIG. 6a shows an oblique view of an alternative embodiment of the osteosynthesis device.
Figure 6B:
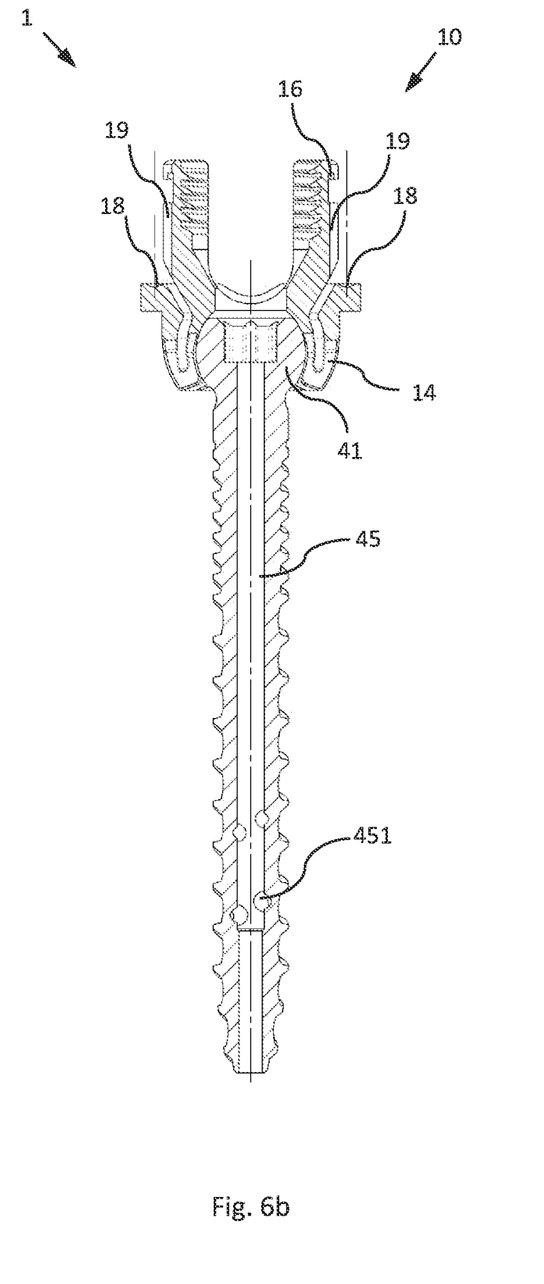
Figure 7A:
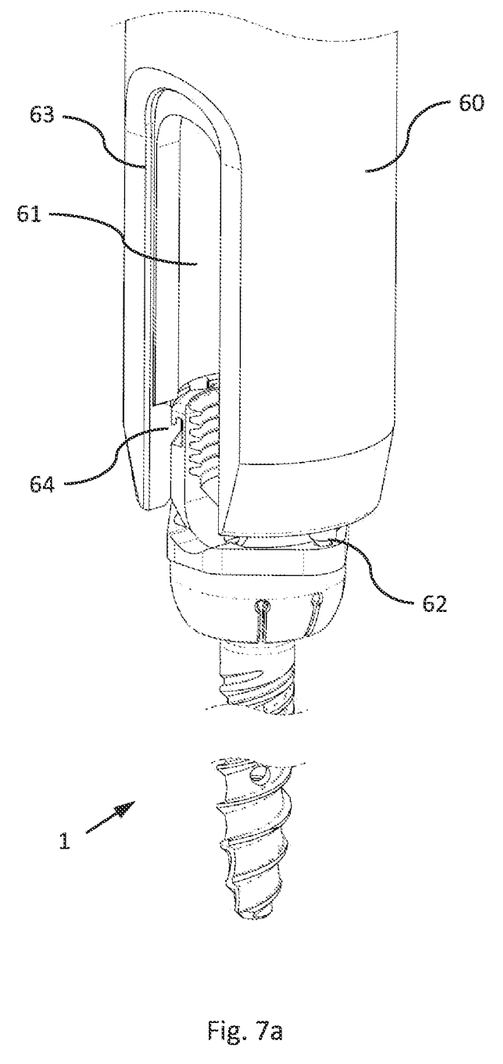
Figure 7B:
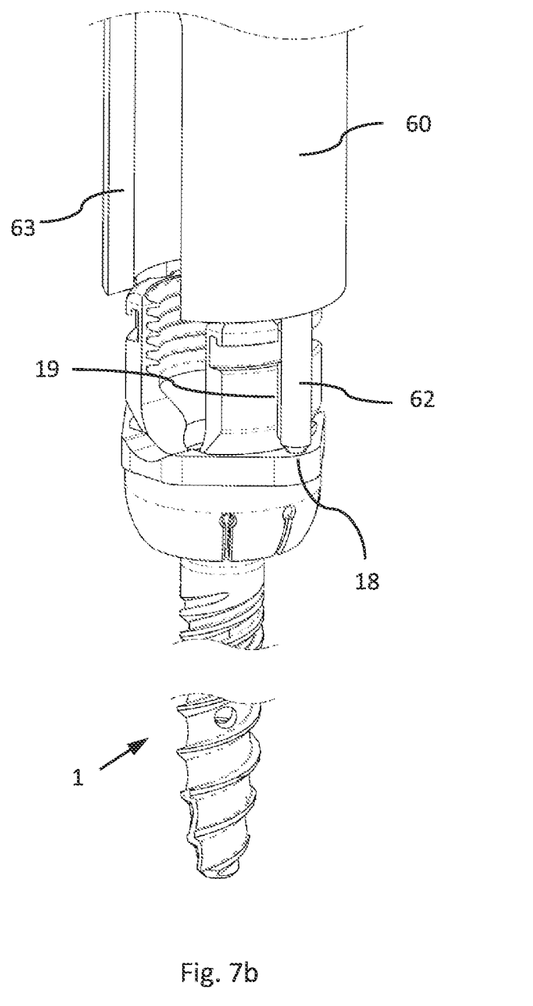
FIG. 7b shows FIG. 7a, albeit with the outer sleeve of the instrument hidden so that the inner instrument sleeve can be seen.
Figure 7C:
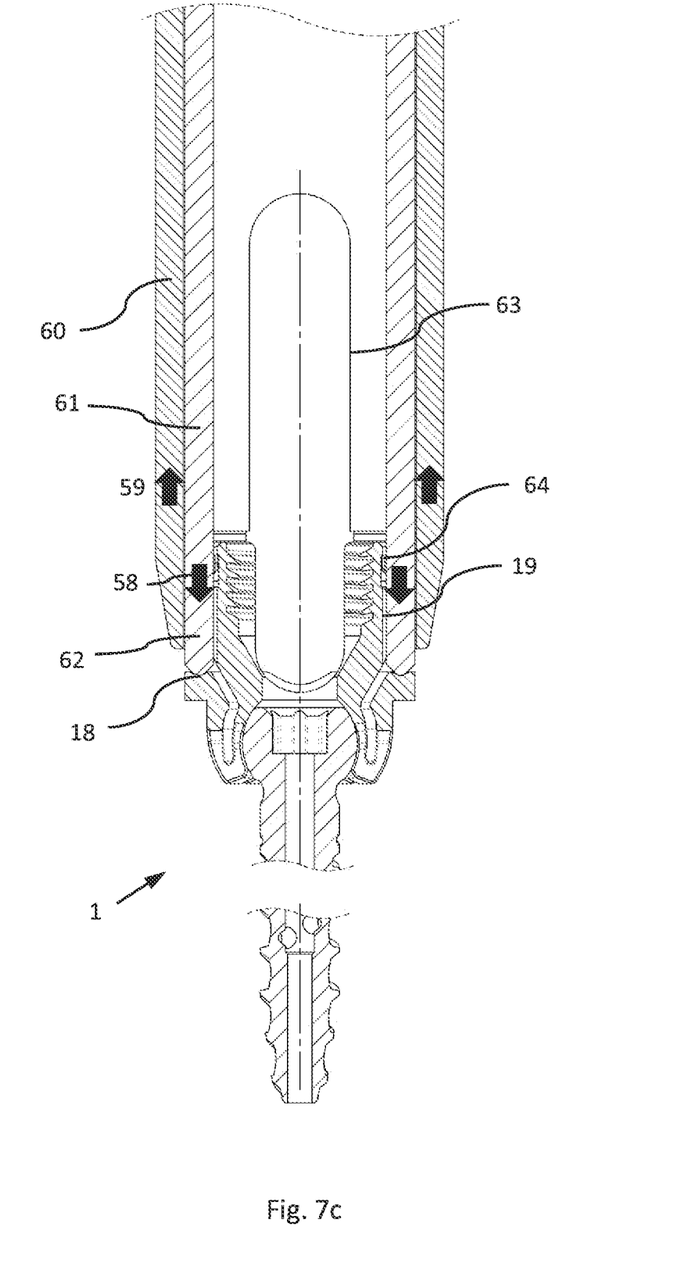
FIG. 7c illustrates a sectional view of FIG. 7b.

In an alternative configuration, at least one additional projection or contact point (18), which is an indirect or direct element of the outer wall (141) and via which a compressive force can be introduced, provides a possibility to effect the clamping of the bone anchor head (41) even without an inserted connecting rod (30) and/or grub screw (20) (FIGS. 6a and 6b). For this purpose, as already described, at least one contact point or projection (18) is provided on the outer wall (141) and at least one additional retaining feature (16) for attaching an instrument (60, 61) is provided on the proximal fork head. A recess (19) is optionally provided on the fork head so that the contact point (18) is accessible for an instrument from the proximal side (101). With the help of an instrument (60, 61) suitable for this purpose, a compressive force (58) can be applied to the contact point (18), the holding feature (16) serving as a counter bearing for the reaction tensile force (59) (FIGS. 7a, 7b and 7c). To initiate a relative movement, the instrument must consist of at least two sleeves (60, 61) which are arranged so as to be displaceable relative to one another. An outer sleeve (60), which can be attached to the retaining feature (16) of the fork head (10) by a suitable engagement feature (64), and an inner sleeve (61), which has corresponding pins or projections (62) and that communicates directly with the contact point (18) and can apply a compressive force, are suitable for this purpose. Optimally, such an instrument has a lateral oval cutout (64) in which a connecting rod can be inserted and guided. Initiation of a pressing force (58) to the contact point (18) creates an angle-stable clamping of the bone anchor (40) in the fork head (10, 13) without a connecting rod (30) and/or a grub screw (20) being present.

The invention claimed is:

1. An osteosynthesis device for the treatment of the spine, comprising:

a fork head which is U-shaped in a side view, and which fork head, in a proximal direction, has two fork legs with an internal thread and in which a connecting rod can be received, a grub screw is passed through the internal thread, and the fork head is detachably connected to a bone anchor, and the bone anchor is pivotably mounted in a ball seat of the fork head, wherein the fork head in the ball seat area has slots open towards a distal side and thereby at least one deflectable leg is formed, characterized in that the fork head with at least one deflectable leg, which can be applied to the outer surface of a bone anchor head, wherein the at least one leg has an outer wall and an inner wall, which are interconnected at at least one point in such a way that upon tightening the grub screw, a pressing against one another of the outer wall and the inner wall from the proximal to the distal direction is generated, so that a compressive stress arises in the outer wall and a tensile stress arises in the inner wall, and wherein between the inner wall and the outer wall, there is a gap which is formed circumferentially, whereby the at least one deflectable leg is forced against an outer circumference of a spherical head and as a result, the spherical head of the bone anchor clamps in the fork head at a stable angle due to a resulting compressive force.

2. The osteosynthesis device according to claim 1, wherein the slots extend from radially inside to radially outside, so that the inner wall, outer wall and the connection point have slots.

3. The osteosynthesis device according to claim 1, wherein the wall thickness of the outer wall is thicker than that of the inner wall.

4. The osteosynthesis device according to claim 1, wherein the inner wall has at least a smallest wall thickness of 0.3 mm and a maximum wall thickness of 1.5 mm.

5. The osteosynthesis device according to claim 1, wherein the outer wall and the inner wall of the deflectable leg are integrally connected to one another at least in the area of the distal free end of the deflectable leg.

6. The osteosynthesis device according to claim 1, wherein the outer wall and inner wall of the deflectable leg are connected to one another by further struts or supports.

7. The osteosynthesis device according to claim 1, wherein the outer wall of the deflectable leg tapers at least in sections from the proximal to the distal side.

8. The osteosynthesis device according to claim 1, wherein the inner wall of the deflectable leg tapers at least in sections from the proximal to the distal side.

9. The osteosynthesis device according to claim 1, wherein the inner wall of the deflectable leg has a radius at the connection point.

10. The osteosynthesis device according to claim 1, wherein inner walls of deflectable legs coming from the distal side merge above the ball seat and form the proximal area and the fork legs.

11. The osteosynthesis device according to claim 1, wherein a proximal area of the outer wall fully encloses the fork head and ends below the proximal end of the fork head.

12. The osteosynthesis device according to claim 1, wherein the at least one deflectable leg is separated by slots, and the slots separate outer wall and inner wall in sections.

13. The osteosynthesis device according to claim 1, wherein the slots of the outer wall have a different height than the slots of the inner wall.

14. The osteosynthesis device according to claim 1, wherein the fork legs are connected to one another in a proximal area and contain the internal thread when connected.

15. The osteosynthesis device according to claim 1, wherein the fork head as a whole is formed integrally.

16. The osteosynthesis device according to claim 1, wherein the fork head is produced by an additive manufacturing process and consists of a metallic alloy consisting of titanium, cobalt-chromium, or stainless steel alloy.

17. The osteosynthesis device according to claim 1, wherein the fork head has at least one distally directed edge or projections in an area of the fully enclosing outer wall, and at least one proximally directed edge or projection can be used as a counter bearing to initiate an opposing force acting thereon that generates a pulling against one another of the outer wall and the inner wall, whereby a compressive stress in the inner wall and a tensile stress in the outer wall lead to the at least one leg moving away from the outer surface of the bone anchor head.

18. The osteosynthesis device according to claim 1, wherein at least one contact point or projection is provided on the outer wall, and at least one retaining feature for the attachment of an instrument is provided on a proximal fork head, and when initiating a pressure force to the contact point an angle-stable clamping of the bone anchor in the fork head is generated without a connecting rod and/or grub screw being present.

19. An osteosynthesis device for the treatment of the spine, comprising a fork head which is U-shaped in a side view, and which fork head, in a proximal direction, has two fork legs with an internal thread and in which a connecting rod can be received, a grub screw is passed through the internal thread, and the fork head is detachably connected to a bone ancho, and the bone anchor is pivotably mounted in a ball seat of the fork head, wherein the fork head in the ball seat area has slots open towards a distal side and thereby at least on deflectable leg is formed, characterized in that the fork head with at least one deflectable leg, which can be applied to the outer surface of a bone anchor head, wherein the at least on leg has an outer wall and an inner wall, which are interconnected at at least one point in such a way that upon tightening the grub screw, a pressing against one another of the outer wall and the inner wall from the proximal to the distal direction is generated, so that a compressive stress arises in the outer wall and a tensile stress arises in the inner wall, wherein the at least on deflectable leg is forced against an outer circumference of a spherical head of the bone anchor and as a result, the spherical head clamps in the fork head at a stable angle due to a resulting compressive force, wherein in an unloaded state the connecting rod rests on at least one outer rod support, the connecting rod being spaced apart from at least one inner rod support, and in a loaded condition with tightened grub screw said spacing is reduced.

* * * * *